US010016311B2

(12) United States Patent
Loyd (10) Patent No.: US 10,016,311 B2
(45) Date of Patent: Jul. 10, 2018

(54) ELASTIC CONTAINED WITHIN A JOINTLY FOLDED TOP COVER AND BOTTOM COVER AND PROCESS OF MAKING

(75) Inventor: Adrienne Loyd, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1711 days.

(21) Appl. No.: 10/310,384

(22) Filed: Dec. 5, 2002

(65) Prior Publication Data
US 2004/0111075 A1 Jun. 10, 2004

(51) Int. Cl.
*A61F 13/15* (2006.01)

(52) U.S. Cl.
CPC .................................. *A61F 13/15* (2013.01)

(58) Field of Classification Search
USPC ............ 604/385.01, 385.23–385.24, 385.27, 604/385.101, 385.16, 385.12, 385.31
See application file for complete search history.

(56) References Cited

U.S. PATENT DOCUMENTS

| 4,579,556 | A | | 4/1986 | McFarland ............... 604/385 A |
|---|---|---|---|---|
| 4,598,528 | A | | 7/1986 | McFarland et al. ............ 53/430 |
| 4,668,230 | A | | 5/1987 | Damico et al. ........... 604/385 A |
| 4,701,177 | A | | 10/1987 | Ellis et al. .................... 604/385 |
| 4,770,657 | A | | 9/1988 | Ellis et al. ................ 604/385 A |
| 4,772,282 | A | | 9/1988 | Oakley ...................... 604/385.1 |
| 4,787,896 | A | * | 11/1988 | Houghton et al. ....... 604/385.23 |
| 4,886,512 | A | | 12/1989 | Damico et al. ........... 609/385.2 |
| 4,944,735 | A | | 7/1990 | Mokry ...................... 604/385.2 |
| 5,032,121 | A | | 7/1991 | Mokry ...................... 604/385.2 |
| 5,074,856 | A | | 12/1991 | Coe et al. ................. 604/385.1 |
| 5,085,564 | A | | 2/1992 | Naylor et al. .................. 418/48 |
| 5,085,654 | A | | 2/1992 | Buell ............................ 604/370 |
| 5,234,422 | A | | 8/1993 | Sneller et al. ............ 604/385.2 |
| 5,295,988 | A | * | 3/1994 | Muckenfuhs et al. ... 604/385.02 |
| 5,387,208 | A | * | 2/1995 | Ashton et al. ............... 604/378 |
| 5,411,498 | A | | 5/1995 | Fahrenkrug et al. ...... 604/385.2 |
| 5,542,941 | A | | 8/1996 | Morita ...................... 604/385.1 |
| 5,558,659 | A | | 9/1996 | Sherrod et al. ......... 604/385.26 |
| 5,613,961 | A | | 3/1997 | DiPalma et al. ............. 604/369 |
| 5,704,931 | A | | 1/1998 | Holtman et al. ............. 604/387 |
| 5,769,835 | A | | 6/1998 | Fell et al. ................. 604/385.2 |
| 5,865,825 | A | | 2/1999 | Schlinz ................... 604/385.201 |
| 6,126,648 | A | | 10/2000 | Keck et al. ............... 604/385.2 |
| 6,231,554 | B1 | | 5/2001 | Menard .................... 604/385.01 |
| 6,833,179 | B2 | * | 12/2004 | May et al. .................... 428/212 |

FOREIGN PATENT DOCUMENTS

| EP | 0972502 | 1/2000 |
|---|---|---|
| EP | 1275359 | 1/2003 |

OTHER PUBLICATIONS

EU Search Report for International Application No. PCT/US 03/18390, (Dec. 9, 2003), 2 pgs.

* cited by examiner

*Primary Examiner* — Jacqueline F. Stephens
(74) *Attorney, Agent, or Firm* — Dority & Manning, P.A.

(57) ABSTRACT

An absorbent article is disclosed. The absorbent article is a pad that includes a top cover and a lower baffle. The absorbent article also includes a shaping element. The shaping element is folded within the top cover and the absorbent article. The fold is directed toward the baffle. The top cover therefore forms a terminal seam on the lower surface of the baffle. A process is also disclosed. The process includes folding the shaping element into the edges of the top cover and the baffle as the top cover and the baffle form a single fold.

20 Claims, 6 Drawing Sheets

ELASTIC CONTAINED WITHIN A JOINTLY FOLDED TOP COVER AND BOTTOM COVER AND PROCESS OF MAKING

TECHNICAL FIELD

Embodiments relate to an article for receiving a liquid. More particularly, embodiments relate to an article for receiving a liquid that is shaped by an elastic shaping element. In particular, an article for receiving a liquid includes a shaping element that is enfolded into both the top cover and the bottom cover.

TECHNICAL BACKGROUND

Many articles used as incontinent products or menstrual pads have been found unsatisfactory as they are bulky and/or ineffective. Many such garments are formed by forming flat sheets into a diaper-like structure for incontinent use. Other pads for catamenial use have been formed in thin flat structures, but these structures have been low in absorption. Further, flat structures have a tendency to wrinkle between the legs during use causing discomfort and distorting the target area where the exudate will be located.

Small elasticized pads have been developed in which an elasticized sanitary napkin is employed. The sanitary napkin has elastic threads that are imbedded in the napkin, running in the long direction of the napkin. Other small elasticized pads have been developed in which a sanitary napkin having elasticized edges and a raised center portion are employed. However, these pads have not found wide acceptance as they are bulky and do not fit the female form to provide both comfort and absorbency.

It has been known in the diaper art to provide diapers that are shaped by having elastic at the edges. However, diaper-like structures are not suitable for use as a catamenial napkin, or for use as an absorbent member for an adult with mild urinary incontinence. They are too large, bulky, and obtrusive to be suitable for such use.

Therefore, there remains a need for a napkin for catamenial and urinary incontinence use that will not bunch during walking and is comfortable.

SUMMARY

An article is disclosed that includes a liquid-permeable top cover and a liquid-impermeable bottom cover. The bottom cover is also referred to as a baffle. Together, the liquid-permeable top cover and the liquid-impermeable bottom cover form an envelope. In one embodiment, at least one of the top cover and the bottom cover includes a terminal edge under the article. The article is also referred to as a pad.

A shaping element is operatively associated with the top cover and the bottom cover. The top cover and the bottom cover are folded over the shaping element. In other words, the shaping element is enfolded with the top cover and the bottom cover in a direction toward the exterior surface of the bottom cover.

An absorbent first element is enclosed by the top cover and the bottom cover. The absorbent first element is a liquid-absorbing medium such as is used in the personal care products arts.

In the personal care products art, the top cover is presented against the user and the bottom cover is presented against the user's clothing such as the user's underwear.

In one embodiment, the shaping element is first secured to the bottom cover, within the fold, by a shaping element adhesive, and second contained within a seam between the top cover and the bottom cover by a construction adhesive. According to an embodiment, since at least one of the top cover and the bottom cover terminates under the pad, the seam likewise is located under the pad.

In one embodiment, the pad curls into an arcuate shape due to the presence of the shaping element when it is allowed to recoil. Additionally, a gathered portion of at least one of the top cover and the bottom cover, forms along the occurrence of the shaping element.

In one embodiment, at least one subsequent shaping element is provided adjacent the first shaping element, and within the fold of the top cover and the bottom cover.

A process is also disclosed. The process includes providing a top cover, providing a bottom cover, and providing a shaping element according to the various article embodiments set forth in this disclosure. The process includes folding the top cover and the bottom cover, in a single fold, after a manner that causes the shaping element to be enfolded with the top cover and the bottom cover in a direction toward the lower exterior surface of the bottom cover.

These and other embodiments are set forth more fully in the balance of the disclosure.

BRIEF DESCRIPTION OF THE DRAWINGS

In order to understand the manner in which embodiments are obtained, a more particular description of various embodiments briefly described above will be rendered by reference to the appended drawings. Understanding that these drawings depict only typical embodiments that are not necessarily drawn to scale and are not therefore to be considered to be limiting of its scope, the embodiments will be described and explained with additional specificity and detail through the use of the accompanying drawings in which.

DETAILED DESCRIPTION

The following description includes terms, such as first, second, etc. that are used for descriptive purposes only and are not to be construed as limiting. In the following detailed description, reference is made to the accompanying drawings, which form a part hereof. These drawings show, by way of illustration, specific embodiments in which the invention may be practiced. In the drawings, some of the like numerals describe substantially similar components throughout the several views. These embodiments are described in sufficient detail to enable those skilled in the art to practice the invention. Other embodiments may be used and structural changes may be made without departing from the scope of the several embodiments.

Figure 1:
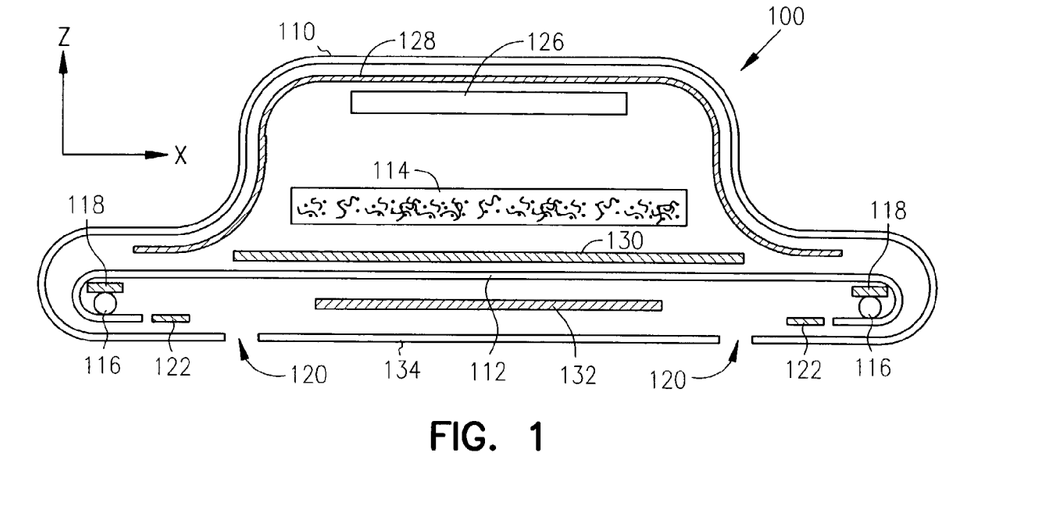
FIG. 1 is a cross section of a pad according to an embodiment.

FIG. 1 is a cross section of a pad according to an embodiment. The pad 100 is in an exploded configuration for clarity. The pad 100 includes a liquid-permeable top cover 110 and a liquid-impermeable bottom cover 112. The bottom cover 112 is also referred to as a baffle. Together, the liquid-permeable top cover 110 and the liquid-impermeable bottom cover 112 form an envelope. In one embodiment, at least one of the top cover 110 and the bottom cover 112 terminates under the pad 100. An absorbent first element 114 is enclosed by the top cover 110 and the bottom cover 112. The absorbent first element 114 is a liquid-absorbing medium such as is used in the personal care products arts.

In one embodiment, the top cover 110 is compliant, soft feeling, and non-irritating to the wearer's skin. Additionally, the top cover 110 is liquid pervious to permit liquids to penetrate through its thickness. In one embodiment, the top cover 110 is manufactured from a wide range of materials such as woven and non-woven materials. In one embodiment, the top cover 110 is derived from polymeric materials such as apertured formed thermoplastic films, apertured plastic films, hydroformed thermoplastic films, and the like. In one embodiment, the top cover 110 is derived from porous foams and the like. In one embodiment, the top cover 110 is derived from reticulated foams and the like. In one embodiment, the top cover 110 is derived from reticulated thermoplastic films and the like. In one embodiment, the top cover 110 is derived from thermoplastic scrims and the like.

Suitable woven and non-woven material embodiments include natural fibers such as wood or cotton fibers and the like. Other suitable woven and non-woven material embodiments include synthetic fibers such as polymeric fibers including polyester, polypropylene, polyethylene fibers, and the like. Other suitable woven and non-woven material embodiments include a combination of natural and synthetic fibers.

In one embodiment, the top cover 110 includes an apertured formed film. An apertured formed film is pervious to body exudates and yet it is non-absorbent and has a reduced tendency to allow liquids to pass back through and re-wet the wearer's skin. Thus, the surface of the formed film which is in contact with the body remains dry, thereby reducing body soiling and creating a more comfortable feel for the wearer.

In one embodiment, the body surface of the top cover 110 is hydrophilic so as to help liquid to transfer through the top cover 110 faster than if the body surface was not hydrophilic so as to diminish the likelihood that fluid will flow off the top cover 110 rather than flowing into and being absorbed by the absorbent core. In one embodiment, surfactant is incorporated into the polymeric materials of the top cover 110.

The bottom cover 112 is impervious to liquids and in one embodiment, is manufactured from a thin plastic film, although other flexible liquid impervious materials can also be used. As used herein, the term "flexible" refers to materials which are compliant and will readily conform to the general shape and contours of the human body. The bottom cover 112 prevents the exudates absorbed and contained in the absorbent first element 114 from wetting articles which contact the sanitary napkin such as pants, pajamas and undergarments. In one embodiment, the bottom cover 112 includes at least one of a woven or non-woven material, polymeric films such as thermoplastic films of polyethylene or polypropylene, or composite materials such as a film-coated non-woven material. In one embodiment, the bottom cover 112 is a polyethylene film having a thickness of from about 0.012 mm (0.5 mil) to about 0.051 mm (2.0 mils). In one embodiment, the bottom cover 112 permits vapors to escape from the absorbent first element 114 while still preventing exudates from passing through the bottom cover 112.

In another embodiment, the top cover 110 is referred to as a top cover 110 including a first liquid permeability. The bottom cover 112 includes a second liquid permeability. In this embodiment, the first liquid permeability is greater than the second liquid permeability. In one embodiment, the bottom cover 112 is porous, but it has at least one of an average pore size or a hydrophobicity which resists the pass-through flow of a liquid that is contemplated for ordinary use. In this embodiment, the bottom cover 112 is substantially liquid impermeable.

In one embodiment, the envelope of the top cover 110 and the bottom cover 112 are referred to as a web. In one embodiment, the web can contain various elements as will be set forth in this disclosure. In one embodiment, the web is an adult care garment precursor or the like, such as for a DEPEND® product or the like, made by Kimberly-Clark Corporation of Neenah, Wis. In one embodiment, the web is a feminine care garment precursor or the like, such as for a KOTEX® product or the like, also made by Kimberly Clark Corporation. In one embodiment, the web is an infant care garment precursor or the like, such as for a HUGGIES® product or the like also made by Kimberly-Clark Corporation. In one embodiment, the web is a childcare garment precursor or the like, such as for a PULL-UPS® product or the like, also made by Kimberly-Clark Corporation. In one embodiment, the web is a non-woven web precursor or the like, such as for a KLEENEX® product or the like, also made by Kimberly-Clark Corporation. In one embodiment, the web is a woven web precursor or the like. By reading this disclosure, it becomes clear that another embodiment includes a "web" that is any other material that is conducive to being processed according to the various embodiments set forth in this disclosure.

In one embodiment, the absorbent first element 114 is any absorbent material which is capable of absorbing or retaining liquids. In one embodiment, the absorbent first element 114 is manufactured in a wide variety of sizes and shapes (e.g., rectangular, oval, hourglass, dog bone, asymmetric, etc.) and from a wide variety of liquid-absorbent materials commonly used in absorbent napkins and other absorbent articles such as comminuted wood pulp which is generally referred to as airlaid.

In one embodiment, the absorbent first element 114 includes creped cellulose wadding and the like. In one embodiment, the absorbent first element 114 includes dmelt-blown polymers including coform and the like. In one embodiment, the absorbent first element 114 includes chemically stiffened, modified or cross-linked cellulosic fibers and the like. In one embodiment, the absorbent first element 114 includes synthetic fibers such as crimped polyester fibers and the like. In one embodiment, the absorbent first element 114 includes peat moss and the like. In one embodiment, the absorbent first element 114 includes tissue including tissue wraps and tissue laminates and the like. In one embodiment, the absorbent first element 114 includes absorbent foams and the like. In one embodiment, the absorbent first element 114 includes absorbent sponges and the like. In one embodiment, the absorbent first element 114 includes superabsorbent polymers and the like. In one embodiment, the absorbent first element 114 includes absorbent gelling materials and the like. In one embodiment, the absorbent first element 114 includes combinations of materials, or mixtures of these.

The configuration and construction of the absorbent first element 114 can also be varied (e.g., the absorbent core can have varying caliper zones such profiled zones (not pictured) so as to be thicker in the center. In one embodiment, the absorbent first element 114 includes a hydrophilic gradient. In one embodiment, the absorbent first element 114 includes a superabsorbent gradient. In one embodiment, the total absorbent capacity of the absorbent first element 114 is compatible with the design loading and the intended use of the pad 100. In one embodiment, the size and absorbent capacity of the absorbent first element 114 can be varied to accommodate different uses such as incontinence pads, pantiliners, regular sanitary napkins, or overnight sanitary napkins.

A first shaping element 116 is operatively associated with the top cover 110 and the bottom cover 112. By "operatively associated", it is meant that the top cover 110 and the bottom cover 112 are folded over the first shaping element 116. The fold is directed downwardly as depicted in FIG. 1 in the negative-Z direction. In other words, the first shaping element 116 is enfolded with the top cover 110 and the bottom cover 112 in a direction toward the bottom cover 112.

In one embodiment, the top cover 110 is presented against the user in the positive-Z direction, and the bottom cover 112 is presented against the user's clothing such as the user's underwear. In one embodiment, the first shaping element 116 is deployed under tension along the Y-axis (see FIG. 3), and it is tensed in order to cause the pad 100 to curl upwardly in the in the positive-Z direction.

In one embodiment, the first shaping element 116 is first secured to the bottom cover 112 by a shaping element adhesive 118, and second contained within a seam 120 between the top cover 110 and the bottom cover 112, by a construction adhesive 122. According to an embodiment, since at least one of the top cover 110 and the bottom cover 112 terminates under the pad 100, the seam 120 likewise is located under the pad 100.

Figure 2B:
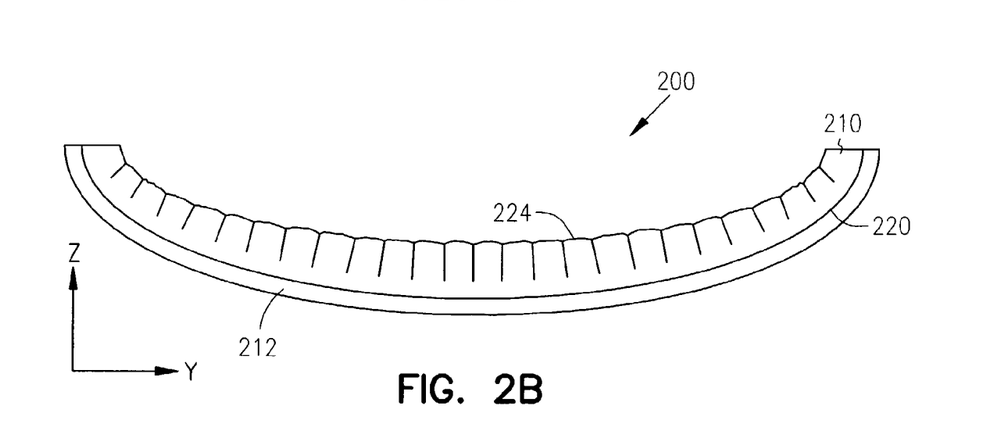
FIG. 2B is a side elevation of the pad depicted in FIG. 2A.
Figure 3:
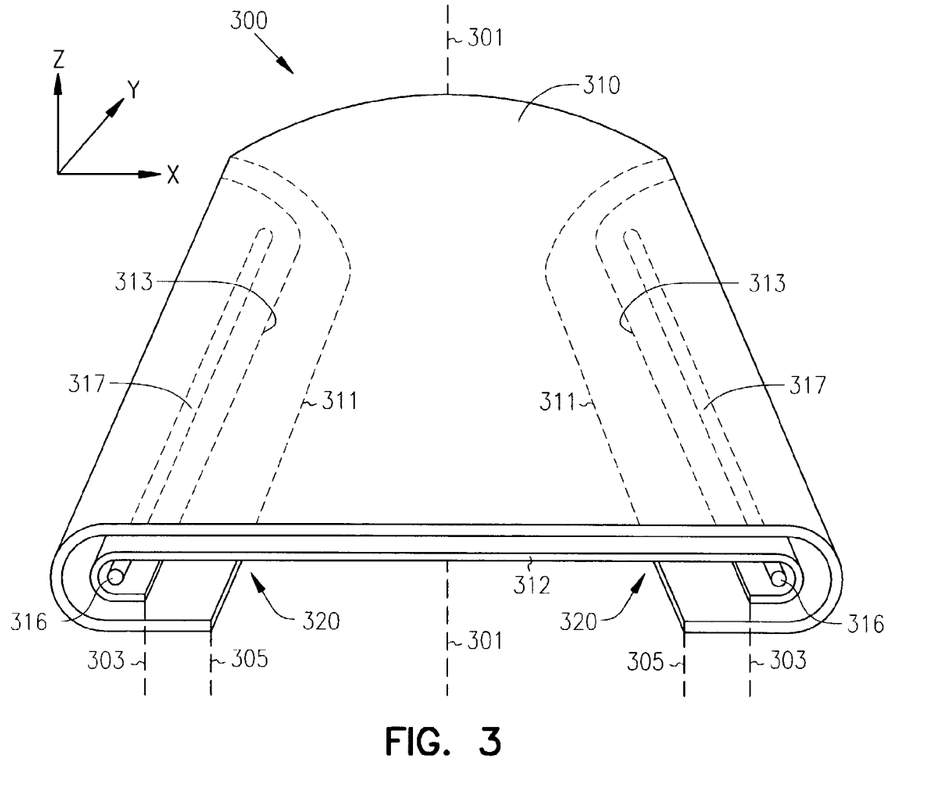
FIG. 3 is partial cut-away perspective elevation of a pad.

In one embodiment, the shaping element adhesive 118 is deployed by intermittent depositions along the pad 100 along the Y-axis (see FIG. 3). An intermittent deposition allows at least one of the top cover 110 and the bottom cover 112 to form a gathered structure that can allow a substantially uniform pucker along the Y-axis of the pad 100 (see FIG. 2B). In one embodiment, a continuous adhesive deposition along the pad 100 is carried out.

Deposition of the shaping element adhesive 118 can be done by various processes. In one embodiment, the shaping element adhesive 118 is air-deposited by a process selected from spraying, meltblowing, swirling, and combinations thereof according to conventional technique. In one embodiment, the shaping element adhesive 118 is contact-deposited by a process selected from slot, bead, Gravure coating, and combinations thereof according to conventional technique.

In one embodiment, the adhesive delivered by the adhesive applicator is any suitable material that can attach the first shaping element 116 to the bottom cover 112. In one embodiment, the adhesive secures a plastic bottom cover 112 to an elastomeric first shaping element 116. Such an adhesive is known in the art. In one embodiment, the adhesive is a water-based composition that is pressure sensitive such as an acrylate adhesive or the like. In one embodiment, the adhesive is a thermoplastic composition that is used to thermally weld structures together. In one embodiment, the thermoplastic adhesive is H2840, manufactured by Findley Adhesives of Wauwatosa, Wis. In one embodiment, the thermoplastic adhesive is NS 34-5610 manufactured by National Starch of Bridgewater, N.J. In one embodiment, the adhesive is a double-sided film such as a double-sided tape, as known in the art.

Figure 2A:
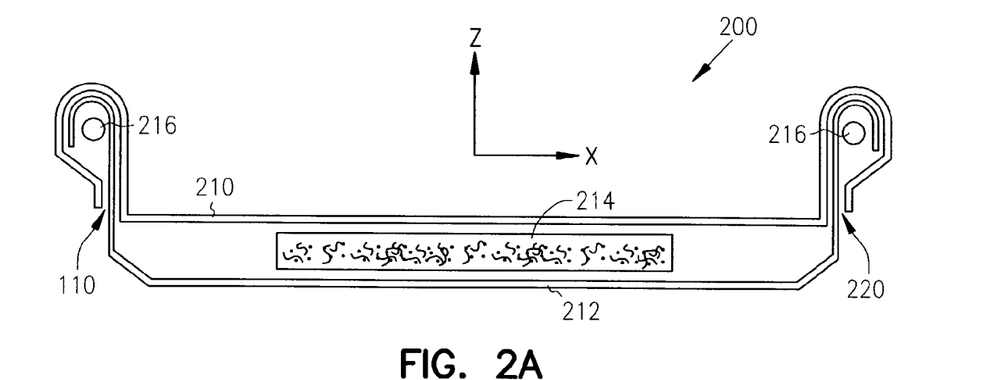
FIG. 2A is a cross section of a pad according to an embodiment.

FIG. 2A is a cross section of a pad according to an embodiment. The pad 200 is depicted in a simplified, schematic view. The pad 200 includes a liquid-permeable top cover 210 and a liquid-impermeable bottom cover 212. The bottom cover 212 is also referred to as a baffle. Together, the liquid-permeable top cover 210 and the liquid-impermeable bottom cover 212 form an envelope. In one embodiment, at least one of the top cover 110 and the bottom cover 212 terminates against the bottom cover 212. An absorbent first element 214 is enclosed by the top cover 210 and the bottom cover 212. The absorbent first element 214 is a liquid-absorbing medium such as is used in the personal care products arts.

FIG. 2A depicts one embodiment where the seam 220 between the edge of the top cover 210 and a portion of the bottom cover 212 have also been drawn into the Z-direction and the pad 200 has partially deflected in a region proximate the first shaping element 216.

FIG. 2B is a side elevation of the pad depicted in FIG. 2A. The depiction in FIG. 2B represents the effect of the first shaping element 216 as it recoils. Thereby, a portion of each of the top cover 210 and bottom cover 212, each containing the first shaping element 216, are drawn into the Z-direction. The portion of the pad 200 that includes the absorbent first element 214 remains relatively unaffected when viewed in this cross section.

In one embodiment, the pad 200 is a side elevation of the pad 100 depicted in FIG. 1, but not in an exploded configuration. The pad 200 is depicted as curling into an arcuate shape in the Z-direction due to the presence of the first shaping element 216 when it is allowed to recoil. The pad 200 also depicts the top cover 210, the bottom cover 212, and the seam 220 therebetween when the seam is drawn also into the Z-direction when the pad 200 has partially deflected in a region proximate the first shaping element 216. The seam 220 is analogous to the seam 120 depicted in FIG. 1, but the portion of the pad 200 that enfolds the first shaping element (not pictured) has folded upwardly in the Z-direction. Accordingly, the seam 220 is revealed in a side elevation.

Additionally, FIG. 2B depicts a gathered portion 224 of at least one of the top cover 210 and the bottom cover 212. In one embodiment, because the first shaping element (not pictured) is fastened to the bottom cover 212 by intermittent depositions of the shaping element adhesive 118 (FIG. 1), the gathered portion 224 forms a substantially uniform pucker. In one embodiment, a continuous adhesive deposition along the pad 200 is carried out.

In one embodiment, the first shaping element 216 (FIG. 2A) is variably tensed along its length. In this embodiment, shaping is controlled to be either along the entire length of the pad 200, or in a portion thereof. In one embodiment, the shaping element 216 causes only a portion of the ends of the pad to curl upwardly in the Z-direction.

Reference is again directed to FIG. 1. In one embodiment, the first shaping element 116 is an organic elastomeric material. An "elastomeric material" is understood to be a material that tends to recover its original size and shape after the removal of a deformational force. In one embodiment, an "elastomeric material" is a material that can be elongated greater than at least one-fourth its original dimension, and can recover toward its original dimension at by least one-tenth.

In one embodiment, the first shaping element 116 is made of fluid permeable materials. In one embodiment, the first shaping element 116 is made of a wet-spun elastomeric material. In one embodiment, the first shaping element 116 is an extruded, hot-melt elastomeric adhesive. In one embodiment, the first shaping element 116 is an adhesive elastomeric foam. In one embodiment, the first shaping element 116 is a stretchable film.

In one embodiment, the first shaping element 116 is an elastic material such as LYCRA® manufactured by E.I. du Pont de Nemours and Company of Delaware. In one embodiment, the first shaping element 116 is a rigid material. In one embodiment, the first shaping element 116 is a stiff member that imparts sufficient rigidity to the pad 100 to cause a selected shape to form.

In one embodiment, the first shaping element 116 is merely fullness of the web that forms at least one of the top cover 110 and the bottom cover 112 as it is processed. In this embodiment, the fullness in the web can be formed by gathering and fastening the web to itself by various methods known in the art such as by a folding and intermeshing by a perforation process, a thermal welding process, or a gluing process. Further, the recoil experienced in the pad 100 is the flexible nature of at least one of the top cover 110 and the bottom cover 112.

In one embodiment, the first shaping element is a combination of at least one of an elastic member, a rigid member, a gathered portion of at least one of the top cover 110 and the bottom cover 112, and a combination thereof.

In one embodiment, a surge element 126 is disposed above the absorbent first element 114. In one embodiment, the surge element 126 is employed for extra liquid-absorption capabilities. The surge element 126 acts as a liquid intake and distribution layer. The pad 100 also includes a top cover adhesive 128 that can make contact with the surge element 126 if present, the absorbent first element 114, and the bottom cover 112. In one embodiment, the top cover adhesive 128 is formed in a swirl pattern, as is known in the art, to allow fluid to penetrate into the surge element 126 and the absorbent first element 114. The pad 100 also includes a baffle adhesive 130 that secures the bottom cover 112 to the absorbent first element 114. The pad 100 also includes a garment adhesive 132 and a release layer 134 that protects the garment adhesive 132 prior to deployment.

FIG. 3 is a partial cut-away perspective elevation of a pad 300 that is presented in a simplified view for clarity. In one embodiment, the pad 300 is presented in a flat configuration. The pad 300 includes a liquid-permeable top cover 310 and a liquid-impermeable bottom cover 312. Together, the liquid-permeable top cover 310 and the liquid-impermeable bottom cover 312 form an envelope. A first shaping element 316 is operatively associated with the top cover 310 and the bottom cover 312.

The pad 300 is configured such that a portion of the top cover 310 and the bottom cover 312 are folded over the first shaping element 316. FIG. 3 also depicts hidden elements. In phantom lines, the terminal edge 311 of the top cover 310 is shown to form a seam 320 against the bottom cover 312. Further, the terminal edge 313 of the bottom cover 312 is also depicted, as well as the hidden portion 317 of the first shaping element 316 as it is deployed substantially parallel to the Y-axis.

In another embodiment, the pad 300 is deployed along a symmetry line 301 and the terminal edge 311 of the top cover 310 terminates at a first coordinate 303 along the X-axis at a first distance from the symmetry line 301. Similarly, the terminal edge 313 of the bottom cover 312 terminates at a second coordinate 305 along the X-axis at a second distance from the symmetry line 301.

Although the embodiment depicted in FIG. 3 illustrates the first coordinate 303 being farther from the symmetry line 301 than the second coordinate 305, another embodiment (not pictured) includes the opposite, such that the edge 313 of the bottom cover 312 terminates closer to the symmetry line 301 than the terminal edge 311 of the top cover. In yet another embodiment, the terminal edges 311 and 313, respectively, terminate (not pictured) at substantially the same distance from the symmetry line 301. Similarly, one embodiment (not pictured) includes the edge 313 of the bottom cover 312 terminating the same distance to the symmetry line 301 as the terminal edge 311 of the top cover.

Figure 4:
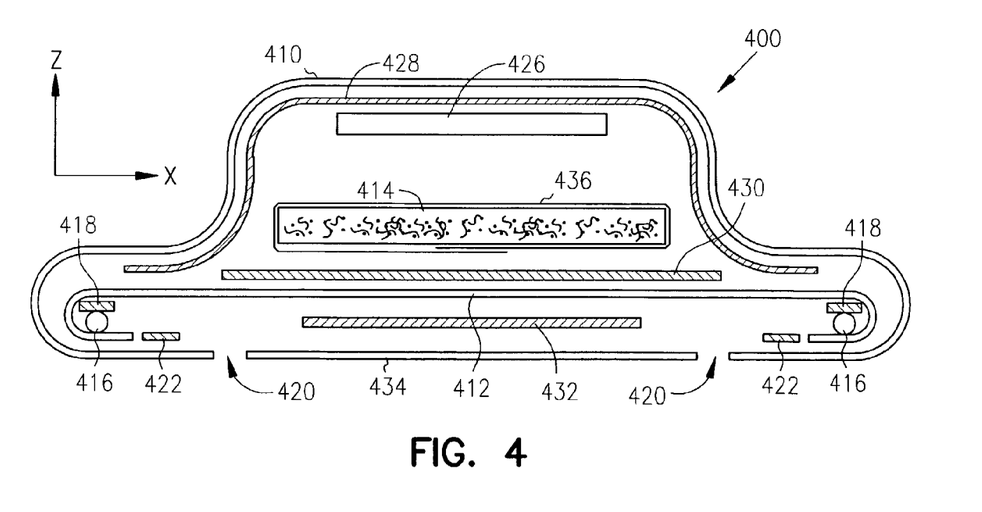
FIG. 4 is a cross section of a pad according to another embodiment.

FIG. 4 is a cross section of a pad according to another embodiment. The pad 400 includes elements and structures similar to the pad 100 depicted in FIG. 1. The pad 400 is in an exploded configuration for clarity. The pad 400 includes a liquid-permeable top cover 410 and a liquid-impermeable bottom cover 412. Together, the liquid-permeable top cover 410 and the liquid-impermeable bottom cover 412 form an envelope. An absorbent first element 414 is enclosed by the top cover 410 and the bottom cover 412. A first shaping element 416 is operatively associated with the top cover 410 and the bottom cover 412. The first shaping element 416 is deployed under tension along the Y-axis (see FIG. 3), and it is tensed in order to cause the pad 400 to curl upwardly in the direction of the Z-axis.

In one embodiment, the first shaping element 416 is first secured to the bottom cover 412 by a shaping element adhesive 418, and second contained within a seam 420 between the top cover 410 and the bottom cover 412 by a construction adhesive 422. In one embodiment, the shaping element adhesive 418 is deployed by intermittent depositions along the pad 400 along the Y-axis (see FIG. 3). An intermittent deposition allows the top cover 410 and the bottom cover 412 to form a gathered structure that can allow a substantially uniform pucker along the Y-axis of the pad 400. In one embodiment, a continuous adhesive deposition along the pad 400 is carried out.

In one embodiment, a surge element 426 is disposed above the absorbent first element 414. The surge element 426 acts as a liquid intake and distribution layer. The pad 400 also includes an upper liner adhesive 428 that can make contact with the surge element 426 if present, the absorbent first element 414, and the bottom cover 412. In one embodiment, the upper liner adhesive 428 is formed in a swirl pattern, as is known in the art, to allow fluid to penetrate into the surge element 426 and the absorbent first element 414. The pad 400 also includes a baffle adhesive 430 that secures the bottom cover 412 to the absorbent first element 414. The pad 400 also includes a garment adhesive 432 and a release layer 434 that protects the garment adhesive 432 prior to deployment.

In one embodiment, the pad 400 also includes a first web 436 that acts as an envelope around the absorbent first element 414. In one embodiment, the first web 436 is a first tissue that is made of a material such as a liquid-absorbing wood fiber base. In one embodiment, the first web 436 is an apertured material similar to the materials described for the top cover 110.

Figure 5:
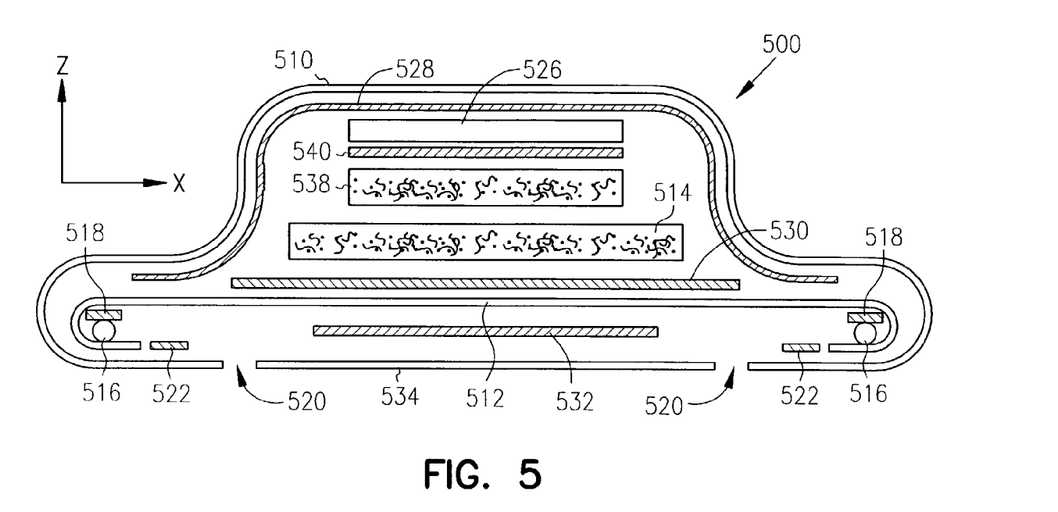
FIG. 5 is a cross section of a pad according to another embodiment.

FIG. 5 is a cross section of a pad according to another embodiment. The pad 500 includes elements and structures similar to the pad 400 depicted in FIG. 4, and some additional elements. The pad 500 is in an exploded configuration for clarity. The pad 500 includes a liquid-permeable top cover 510 and a liquid-impermeable bottom cover 512. An absorbent first element 514 is enclosed by the top cover 510 and the bottom cover 512. A first shaping element 516 is operatively associated with the top cover 510 and the bottom cover 512. The first shaping element 516 is deployed under tension along the Y-axis (see FIG. 3), and it is tensed in order to cause the pad 500 to curl upwardly in the direction of the Z-axis (see FIG. 2).

In one embodiment, the first shaping element 516 is first secured to the bottom cover 512 by a shaping element adhesive 518, and second contained within a seam 520 between the top cover 510 and the bottom cover 512 by a construction adhesive 522. In one embodiment, the shaping element adhesive 518 is deployed by intermittent depositions along the pad 500 along the Y-axis (see FIG. 3). An intermittent deposition allows the top cover 510 and the bottom cover 512 to form a gathered structure that can allow a substantially uniform pucker along the Y-axis of the pad 500. In one embodiment, a continuous adhesive deposition along the pad 500 is carried out.

In one embodiment, a surge element 526 is disposed above the absorbent first element 514. The surge element 526 acts as a liquid intake and distribution layer. The pad 500 also includes an upper liner adhesive 528 that can make contact with the surge element 526 if present, the absorbent first element 514, and the bottom cover 512. In one embodiment, the upper liner adhesive 528 is formed in a swirl pattern, as is known in the art, to allow fluid to penetrate into the surge element 526 and the absorbent first element 514.

Additionally the pad 500 includes an absorbent second element 538 and optionally, a surge element-absorbent second element adhesive 540 disposed in a swirl pattern above the absorbent second element 538. Adhesion of the absorbent second element 538 to the optional surge element 526 can optionally be carried out by a perforation process that can include the top cover 510. The perforation process (not pictured) includes a perforation through selected elements that cause fibers or other structures of elements to intermesh with sufficient adhesion for ordinary use. Such perforation and intermeshing is known in the art.

The pad 500 also includes a baffle adhesive 530 that secures the bottom cover 512 to the absorbent first element 514. The pad 500 also includes a garment adhesive 532 and a release layer 534 that protects the garment adhesive 532 prior to deployment.

Figure 6:
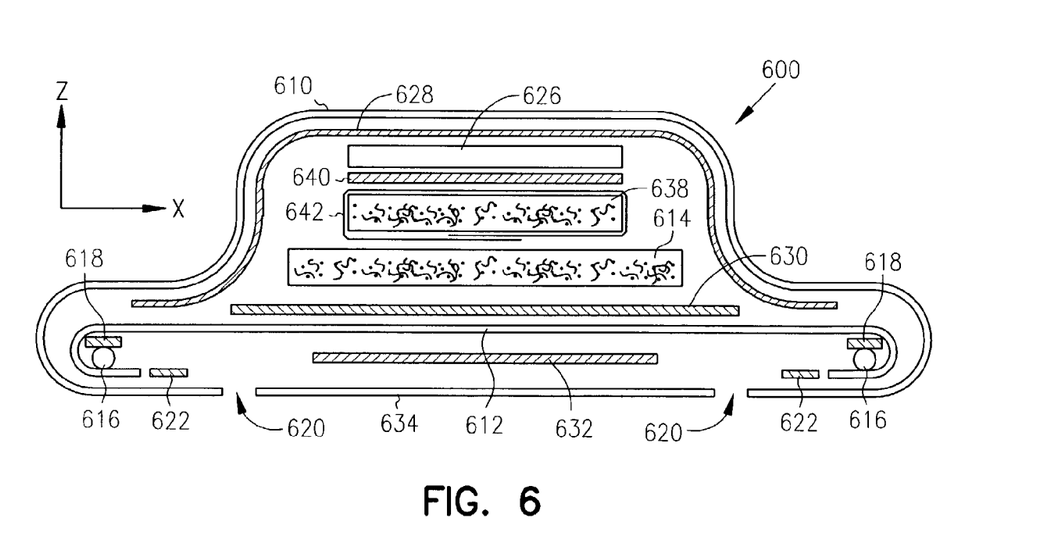
FIG. 6 is a cross section of a pad according to another embodiment.

FIG. 6 is a cross section of a pad according to another embodiment. The pad 600 includes elements and structures similar to the pad 500 depicted in FIG. 5, and some additional elements. The pad 600 is in an exploded configuration for clarity. The pad 600 includes a liquid-permeable top cover 610 and a liquid-impermeable bottom cover 612. An absorbent first element 614 is enclosed by the top cover 610 and the bottom cover 612. A first shaping element 616 is operatively associated with the top cover 610 and the bottom cover 612. The first shaping element 616 is deployed under tension along the Y-axis (see FIG. 3), and it is tensed in order to cause the pad 600 to curl upwardly in the direction of the Z-axis (see FIG. 2).

In one embodiment, the first shaping element 616 is first secured to the bottom cover 612 by a shaping element adhesive 618, and second contained within a seam 620 between the top cover 610 and the bottom cover 612 by a construction adhesive 622. In one embodiment, the shaping element adhesive 618 is deployed by intermittent depositions along the pad 600 along the Y-axis (see FIG. 3). An intermittent deposition allows the top cover 610 and the bottom cover 612 to form a gathered structure that can allow a substantially uniform pucker along the Y-axis of the pad 600. In one embodiment, a continuous adhesive deposition along the pad 600 is carried out.

In one embodiment, a surge element 626 is disposed above the absorbent first element 614. The surge element 626 acts as a liquid intake and distribution layer. The pad 600 also includes an upper liner adhesive 628 that can make contact with the surge element 626 if present, the absorbent first element 614, and the bottom cover 612. In one embodiment, the upper liner adhesive 628 is formed in a swirl pattern, as is known in the art, to allow fluid to penetrate into the surge element 626 and the absorbent first element 614.

Additionally the pad 600 includes an absorbent second element 638 and optionally, a surge element-absorbent second element adhesive 640 disposed in a swirl pattern above the absorbent second element 640. Adhesion of the absorbent second element adhesive 640 to the optional surge element 626 can optionally be carried out in lieu of the surge element-absorbent second element adhesive 640 by a perforation process that can include the top cover 610. The perforation process (not pictured) includes a perforation through selected elements that cause fibers or other structures of elements to intermesh with sufficient adhesion for ordinary use. Such perforation and intermeshing is known in the art.

The pad 600 also includes a baffle adhesive 630 that secures the bottom cover 612 to the absorbent first element 614. The pad 600 also includes a garment adhesive 632 and a release layer 634 that protects the garment adhesive 632 prior to deployment.

In one embodiment, the pad 600 also includes a second web 642 that acts as an envelope around the absorbent second element 638. In one embodiment, the second web 642 is a second tissue that is made of a material such as a liquid-absorbing wood fiber base. In one embodiment, the second web 642 is an apertured material similar to the materials described for the top cover 110.

Figure 7:
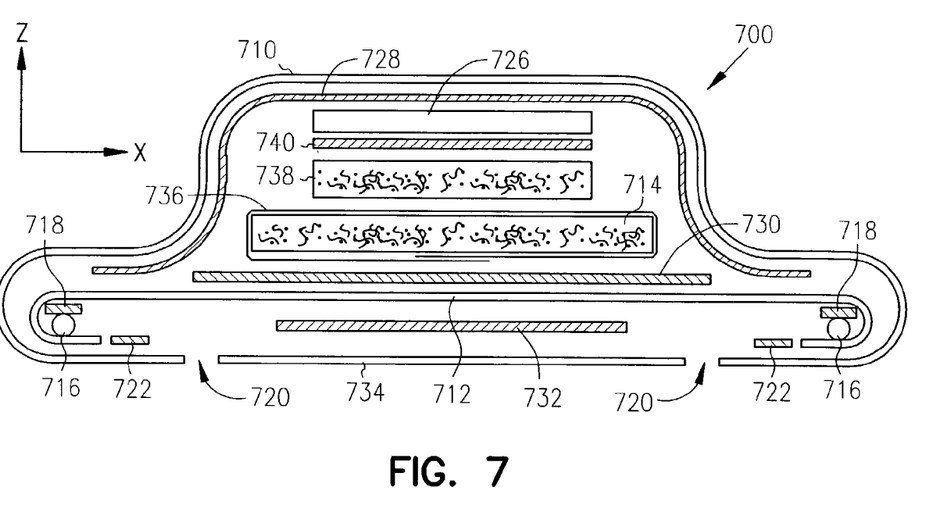
FIG. 7 is a cross section of a pad according to another embodiment.

FIG. 7 is a cross section of a pad according to another embodiment. The pad 700 includes elements and structures similar to the pad 500 depicted in FIG. 5, and some additional elements. The pad 700 is in an exploded configuration for clarity. The pad 700 includes a liquid-permeable top cover 710 and a liquid-impermeable bottom cover 712. An absorbent first element 714 is enclosed by the top cover 710 and the bottom cover 712. A first shaping element 716 is operatively associated with the top cover 710 and the bottom cover 712. The first shaping element 716 is deployed under tension along the Y-axis (see FIG. 3), and it is tensed in order to cause the pad 700 to curl upwardly in the direction of the Z-axis (see FIG. 2).

In one embodiment, the first shaping element 716 is first secured to the bottom cover 712 by a shaping element adhesive 718, and second contained within a seam 720 between the top cover 710 and the bottom cover 712 by a construction adhesive 722. In one embodiment, the shaping element adhesive 718 is deployed by intermittent depositions along the pad 700 along the Y-axis (see FIG. 3). An intermittent deposition allows the top cover 710 and the bottom cover 712 to form a gathered structure that can allow a substantially uniform pucker along the Y-axis of the pad 700. In one embodiment, a continuous adhesive deposition along the pad 700 is carried out.

In one embodiment, a surge element 726 is disposed above the absorbent first element 714. The surge element 726 acts as a liquid intake and distribution layer. The pad 700 also includes an upper liner adhesive 728 that can make contact with the surge element 726 if present, the absorbent first element 714, and the bottom cover 712. In one embodiment, the upper liner adhesive 728 is formed in a swirl pattern, as is known in the art, to allow fluid to penetrate into the surge element 726 and the absorbent first element 714.

Additionally the pad 700 includes an absorbent second element 738 and optionally, a surge element-absorbent second element adhesive 740 disposed in a swirl pattern above the absorbent second element 738. Adhesion of the absorbent second element 738 to the optional surge element 726 can optionally be carried out in lieu of the surge element-absorbent second element adhesive 740 by a perforation process that can include the top cover 710. The perforation process (not pictured) includes a perforation through selected elements that cause fibers or other structures of elements to intermesh with sufficient adhesion for ordinary use. Such perforation and intermeshing is known in the art.

The pad 700 also includes a baffle adhesive 730 that secures the bottom cover 712 to the absorbent first element 714. The pad 700 also includes a garment adhesive 732 and a release layer 734 that protects the garment adhesive 732 prior to deployment.

In one embodiment, the pad 700 also includes a first web 736 that acts as an envelope around the absorbent first element 714. In one embodiment, the first web 736 is a first tissue that is made of a material such as a liquid-absorbing wood fiber base. In one embodiment, the first web 736 is an apertured material similar to the materials described for the top cover 110.

Figure 8:
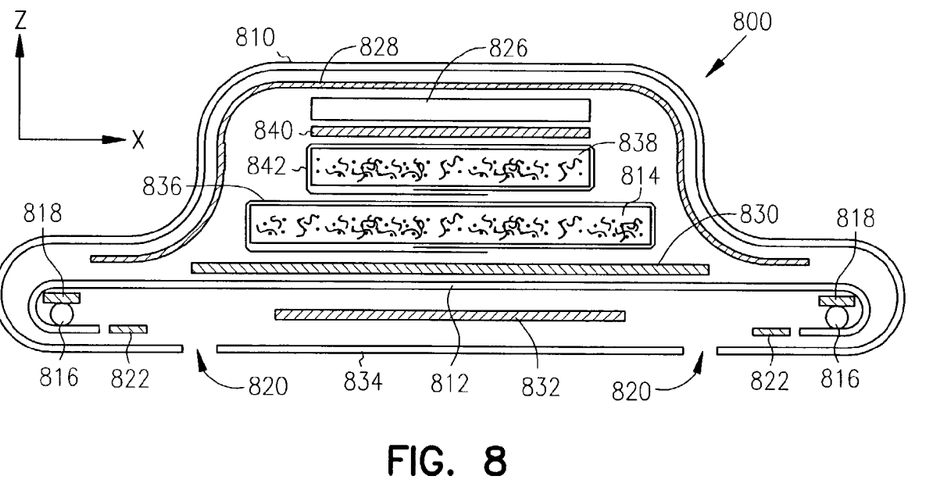
FIG. 8 is a cross section of a pad according to another embodiment.

FIG. 8 is a cross section of a pad according to another embodiment. The pad 800 includes elements and structures similar to the pad 700 depicted in FIG. 7, and some additional elements. The pad 800 is in an exploded configuration for clarity. The pad 800 includes a liquid-permeable top cover 810 and a liquid-impermeable bottom cover 812. An absorbent first element 814 is enclosed by the top cover 810 and the bottom cover 812. A first shaping element 816 is operatively associated with the top cover 810 and the bottom cover 812. The first shaping element 816 is deployed under tension along the Y-axis (see FIG. 3), and it is tensed in order to cause the pad 800 to curl upwardly in the direction of the Z-axis (see FIG. 2).

In one embodiment, the first shaping element 816 is first secured to the bottom cover 812 by a shaping element adhesive 818, and second contained within a seam 820 between the top cover 810 and the bottom cover 812 by a construction adhesive 822. In one embodiment, the shaping element adhesive 818 is deployed by intermittent depositions along the pad 800 along the Y-axis (see FIG. 3). An intermittent deposition allows the top cover 810 and the bottom cover 812 to form a gathered structure that can allow a substantially uniform pucker along the Y-axis of the pad 800. In one embodiment, a continuous adhesive deposition along the pad 800 is carried out.

In one embodiment, a surge element 826 is disposed above the absorbent first element 814. The surge element 826 acts as a liquid intake and distribution layer. The pad 800 also includes an upper liner adhesive 828 that can make contact with the surge element 826 if present, the absorbent first element 814, and the bottom cover 812. In one embodiment, the upper liner adhesive 828 is formed in a swirl pattern, as is known in the art, to allow fluid to penetrate into the surge element 826 and the absorbent first element 814.

Additionally the pad 800 includes an absorbent second element 838 and optionally, a surge element-absorbent second element adhesive 840 disposed in a swirl pattern above the absorbent second element 838. Adhesion of the absorbent second element 838 to the optional surge element 826 can optionally be carried out in lieu of the surge element-absorbent second element adhesive 840 by a perforation process that can include the top cover 810. The perforation process (not pictured) includes a perforation through selected elements that cause fibers or other structures of elements to intermesh with sufficient adhesion for ordinary use. Such perforation and intermeshing is known in the art.

The pad 800 also includes a baffle adhesive 830 that secures the bottom cover 812 to the absorbent first element 814. The pad 800 also includes a garment adhesive 832 and a release layer 834 that protects the garment adhesive 832 prior to deployment.

In one embodiment, the pad 800 also includes a first web 836 that acts as an envelope around the absorbent first element 814. In one embodiment, the first web 836 is a first tissue that is made of a material such as a liquid-absorbing wood fiber base. In one embodiment, the first web 836 is an apertured material similar to the materials described for the top cover 110.

In one embodiment, the pad 800 also includes a second web 842 that acts as an envelope around the absorbent second element 838. In one embodiment, the second web 842 is a second tissue that is made of a material such as a liquid-absorbing wood fiber base. In one embodiment, the second web 842 is an apertured material similar to the materials described for the top cover 110.

Figure 9A:
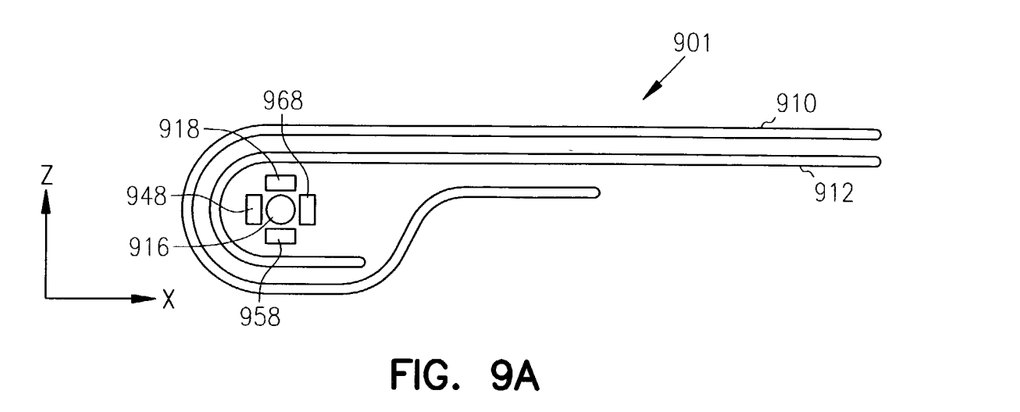
FIGS. 9A-9C are cross-section details of a shaping element or shaping elements according to various embodiments.
Figure 9B:
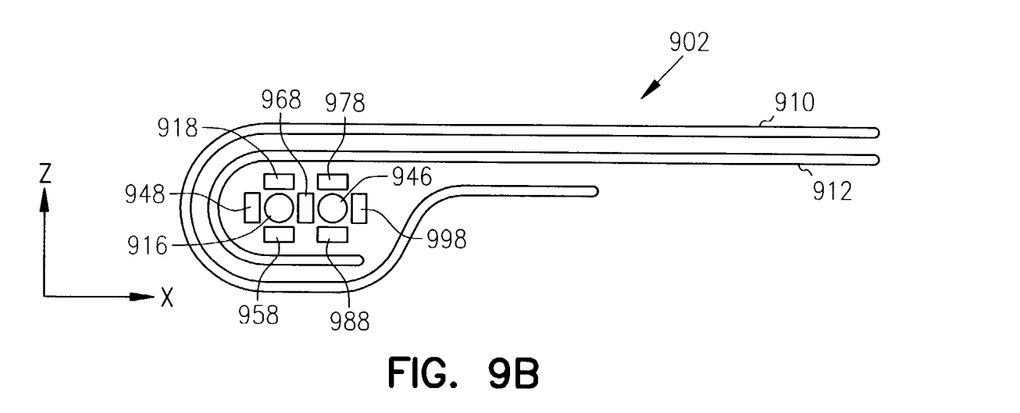
Figure 9C:
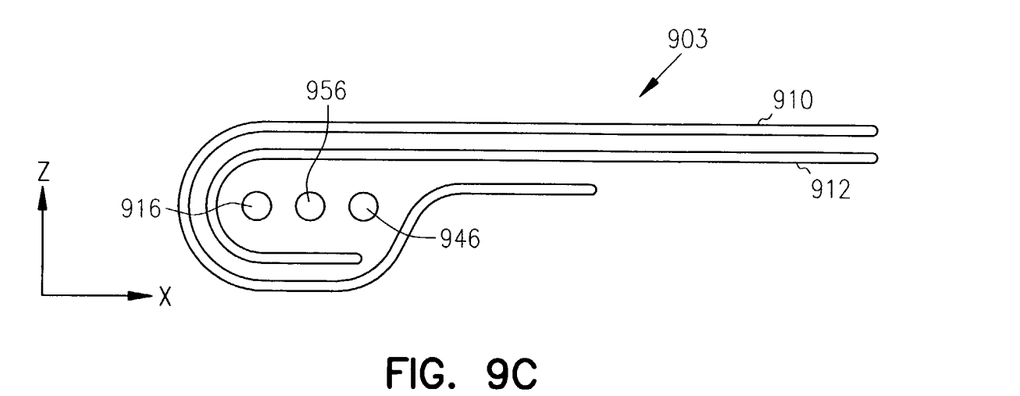

FIGS. 9A-9C are cross-section details of a shaping element or shaping elements according to various embodiments.

FIG. 9A illustrates a section of a pad 901 that includes a top cover 910, a bottom cover 912, and a first shaping element 916. The first shaping element 916 is first secured to the bottom cover 912 by at least one shaping element adhesive 918, 948, 958, and 968. In one embodiment, two of the disclosed shaping element adhesives are included. Alternatively, where two of the shaping element adhesives are disclosed, the first shaping element 916 is contacted with shaping element adhesive on two sides in reference to the X-Z coordinates. In one embodiment, three of the disclosed shaping element adhesives are included. Alternatively, where three of the shaping element adhesives are disclosed, the first shaping element 916 is contacted with shaping element adhesive on three sides in reference to the X-Z coordinates. In one embodiment, all four of the shaping element adhesives are included. Alternatively, where all four of the shaping element adhesives are disclosed, the first shaping element 916 is contacted with shaping element adhesive on all four sides in reference to the X-Z coordinates.

FIG. 9B illustrates a section of a pad 902 that includes a top cover 910, a bottom cover 912, and a first shaping element 916, and a last shaping element 946. The first shaping element 916 and the last shaping element 946 are first secured to the bottom cover 912 by at least one shaping element adhesive 918, 948, 958, 968, 978, 988, and 998. Similar to the embodiment depicted in FIG. 9A, various embodiments include one of the shaping elements, or any combination of the shaping elements depicted in FIG. 9B.

Alternatively similar to the embodiments depicted in FIG. 9A, at least one—and up to all of the surfaces of the first shaping element 916 or the last shaping element 946 is contacted with a shaping element adhesive in reference to the X-Z coordinates.

FIG. 9C illustrates a plurality of more than two shaping elements. In this embodiment, however, as few as one shaping element is present. In one embodiment, a first shaping element 916 is accompanied by a subsequent shaping element 956, and a last shaping element 946. In one embodiment, adhesion of the shaping elements 916, 956, and 946 includes at least one shaping element adhesive similar to the embodiments depicted in FIG. 9B.

In one embodiment, adhesion of the shaping elements 916, 956, and 946 includes a heat process which at least partially fuses at least one of the shaping elements. In one embodiment, adhesions of the shaping elements 916, 956, and 946 include a heat process which at least partially fuses at least one of the shaping elements, and the formation of shaping element adhesive according to the various embodiments set forth in this disclosure.

In one embodiment, such as the embodiments depicted in FIGS. 9B and 9C, the plurality of shaping elements are under tension differently from each other. In one embodiment, the first shaping element 916 is under tension greater than the last shaping element 946. In one embodiment, last shaping element 946 is under tension greater than the first shaping element 916. By varying the tensions in the plurality of shaping elements, specific shaping can be achieved for the pad according to an application.

Figure 10:
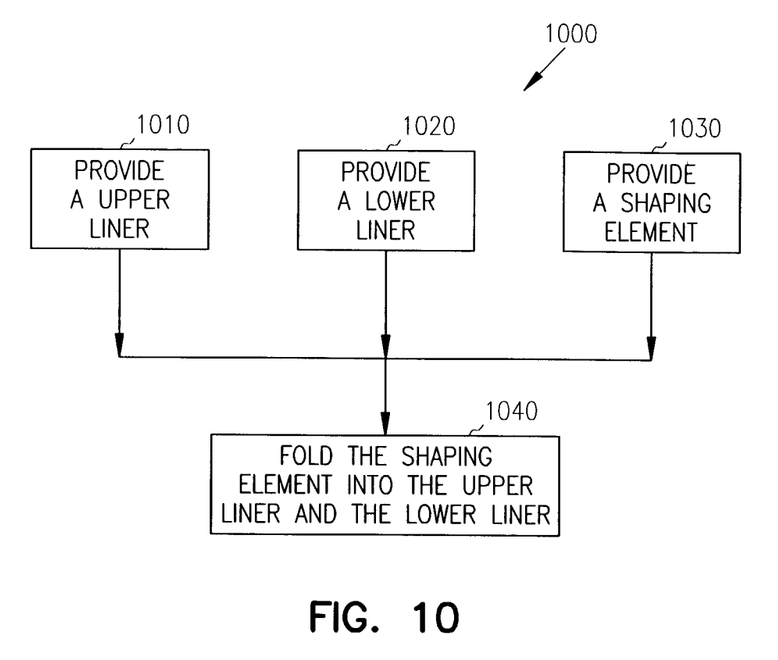
FIG. 10 is a process flow diagram according to an embodiment.

FIG. 10 is a process flow diagram according to an embodiment. It is noted in one embodiment that the shaping element adhesive is disposed above the shaping element (see FIGS. 1 and 4-9). The shaping element adhesive, however, as set forth for the embodiments depicted in FIGS. 9A-9C, can be below the shaping element, or the shaping element adhesive can be on any and/or all sides of the shaping element depending upon the process that is selected for assembling a given pad.

The process 1000 implements the embodiments set forth herein. At 1010, the process includes providing a top cover. At 1020, the process includes providing a bottom cover. At 1030, the process includes providing a shaping element according to the various embodiments set forth in this disclosure. At 1040, the process includes folding the top cover and the bottom cover, in a single fold, after a manner that causes the shaping element to be enfolded with the top cover and the bottom cover in a direction toward the bottom cover. By "enfolded with the top cover and the bottom cover in a direction toward the bottom cover", it is meant that the top cover and the bottom cover each have terminal edges beneath the pad.

Reference is made to FIG. 3. In FIG. 3, it can be seen that the top cover 310 has a terminal edge 311 beneath the pad 300. Similarly, the bottom cover 312 has a terminal edge 313 beneath the pad 300. In another embodiment, "enfolded with the top cover and the bottom cover in a direction toward the bottom cover" means that a seam is formed beneath the pad. Reference is again made to FIG. 3. In FIG. 3, it can be seen that the top cover 310 forms a seam 320 beneath the pad 300.

In one process embodiment, the bottom cover is fed from a web such as a roll, and is first wrapped around the shaping element by a first folding mechanism. Thereafter, the top cover is conjoined with the bottom cover and is second wrapped around the shaping element by a second folding mechanism. In another process embodiment, the bottom cover and the top cover are substantially simultaneously folded by a single folding mechanism.

It is emphasized that the Abstract is provided to comply with 37 C.F.R. §1.72(b) requiring an Abstract that will allow the reader to quickly ascertain the nature and gist of the technical disclosure. It is submitted with the understanding that it will not be used to interpret or limit the scope or meaning of the claims In the foregoing Detailed Description, various features are grouped together in a single embodiment for the purpose of streamlining the disclosure. This method of disclosure is not to be interpreted as reflecting an intention that the claimed embodiments of the invention require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate preferred embodiment It will be readily understood to those skilled in the art that various other changes in the details, material, and arrangements of the parts and method stages which have been described and illustrated in order to explain the nature of this invention may be made without departing from the principles and scope of the invention as expressed in the subjoined claims.

What is claimed is:

1. An article comprising:
    a liquid-permeable top cover;
    a liquid-impermeable bottom cover;
    an absorbent first element enclosed by the top cover and the bottom cover; and
    a first shaping element wherein the top cover and the bottom cover are folded over the first shaping element, and wherein at least one of the top cover and the bottom cover includes a terminal edge under the article.

2. The article according to claim 1, wherein the first shaping element is first secured to the bottom cover, and second contained within a seam between a terminal edge of the top cover and portion of the bottom cover.

3. The article according to claim 1, wherein the first shaping element is selected from an elastic member, a rigid member, a gathered portion of at least one of the top cover and the bottom cover, and a combination thereof.

4. The article according to claim 1, wherein the absorbent first element is enclosed in a first web.

5. The article according to claim 1, further including:
    an absorbent second element above the absorbent first element, and below the liquid-permeable top cover.

6. The article according to claim 1, further including:
    an absorbent second element above the absorbent first element, and below the liquid-permeable liner, wherein the absorbent second element is enclosed in a second web.

7. The article according to claim 1, further including:
    a surge element disposed above the absorbent first element.

8. The article according to claim 1, further including:
    a surge element disposed above the absorbent first element; and
    an absorbent second element above the absorbent first element, and below the liquid-permeable top cover, wherein the first shaping element is an elastic member that is first secured to the bottom cover, and second contained within a seam between the top cover and the bottom cover.

9. An article comprising:
a top cover including a first liquid permeability;
a bottom cover including a second liquid permeability, wherein the first liquid permeability is greater than the second permeability;
an absorbent first element enclosed by the top cover and the bottom cover; and
a first shaping element wherein the first shaping element is enfolded with the top cover and the bottom cover, and wherein at least one of the top cover and the bottom cover includes a terminal edge under the article.

10. The article according to claim 9, wherein the top cover is liquid pervious, wherein the bottom cover is liquid impervious, and wherein the bottom cover is vapor pervious.

11. The article according to claim 9, wherein the first shaping element is first secured to the bottom cover, and second contained within a seam between the top cover and the bottom cover.

12. The article according to claim 9, wherein the first shaping element is selected from an elastic member, a rigid member, a gathered portion of at least one of the top cover and the bottom cover, and a combination thereof.

13. The article according to claim 9, wherein the first shaping element is secured to the bottom cover by at least one selected from an adhesive, and a thermal weld.

14. The article according to claim 9, further including:
at least one subsequent shaping element disposed adjacent the first shaping element, wherein the at least one subsequent shaping element is enfolded with the top cover and the bottom cover.

15. The article according to claim 9, further including:
at least one subsequent shaping element disposed adjacent the first shaping element, wherein the at least one subsequent shaping element is enfolded with the top cover and the bottom cover, wherein the first shaping element is under a first tension, wherein the at least one subsequent shaping element is under a second tension, and wherein the first tension is greater than the second tension.

16. The article according to claim 9, further including:
at least one subsequent shaping element disposed adjacent the first shaping element, wherein the at least one subsequent shaping element is enfolded with the top cover and the bottom cover, wherein the first shaping element is under a first tension, wherein the at least one subsequent shaping element is under a second tension, and wherein the second tension is greater than the first tension.

17. The article according to claim 9, further including:
a surge element disposed above the absorbent first element; and
an absorbent second element above the absorbent first element, and below the liquid-permeable liner, wherein the first shaping element is an elastic member this is first secured to the bottom cover, and second contained within a seam between the top cover and the bottom cover.

18. The article according to claim 9, further including:
at least one subsequent shaping element disposed adjacent the first shaping element, wherein the at least one subsequent shaping element is enfolded with the top cover and the bottom cover, and wherein the first shaping element and the at least one subsequent shaping element are secured by at least one of an adhesive thermal weld.

19. The article according to claim 18, wherein the first shaping element is under a first tension, wherein the at least one subsequent shaping element is under a second tension, and wherein the first tension is greater than the second tension.

20. The article according to claim 18, wherein the at least one subsequent shaping element is under a first tension, wherein the first shaping element is under a second tension, and wherein the second tension is greater than the first tension.

* * * * *